United States Patent [19]

Kitzinger

[11] 4,223,549
[45] Sep. 23, 1980

[54] OXYGEN MONITORING CIRCUIT WITH BUILT IN TESTING MEANS

[75] Inventor: Frank Kitzinger, Montreal, Canada

[73] Assignee: Noranda Mines Limited, Toronto, Canada

[21] Appl. No.: 12,818

[22] Filed: Feb. 16, 1979

[51] Int. Cl.³ .......................................... G01N 27/28
[52] U.S. Cl. ................................... 73/1 R; 73/1 G; 73/19; 73/343 R; 204/195 R
[58] Field of Search .......................... 73/19, 1 R, 1 G; 204/195 R, 195 S

[56] References Cited

U.S. PATENT DOCUMENTS

| 3,957,592 | 5/1976 | Young | 204/195 R |
| 3,979,665 | 9/1976 | Ebling | 204/195 S |
| 4,003,814 | 1/1977 | Tarassoff et al. | 204/195 S |
| 4,094,186 | 6/1978 | Wessel | 73/1 G |

FOREIGN PATENT DOCUMENTS 990352  6/1976  Canada .

Primary Examiner—S. Clement Swisher
Attorney, Agent, or Firm—Fleit & Jacobson

[57] ABSTRACT

An oxygen monitoring circuit is disclosed. The circuit comprises a high impedance follow and hold circuit adapted for connection to an oxygen probe, a readout unit connected to the high impedance follow and hold circuit, a programmer normally connecting the oxygen probe to the high impedance follow and hold circuit but momentarily disconnecting the oxygen probe from the high impedance follow and hold circuit for a relatively short time interval and loading it with a resistor having an impedance relatively higher than the normal impedance of the probe, and a probe failure indicator connected to the outputs of the oxygen probe and of the high impedance follow and hold circuit for detecting any significant change in impedance of the probe and resistor combination as a result of loading and for operating an alarm when the impedance of the probe exceeds a predetermined value.

10 Claims, 5 Drawing Figures

OXYGEN MONITORING CIRCUIT WITH BUILT IN TESTING MEANS

This invention relates to an oxygen probe system for monitoring the oxygen content and temperature of molten metal and, more particularly, to a monitoring circuit which can detect aging of the oxygen probe and warn an operator of impending probe failure.

It is well known to use probes based on galvanic or electromotive cells employing solid electrolytes for measuring the oxygen content of molten metal, such as copper. Some of these probes do not stand the operative conditions of the molten metal more than a few seconds and are discarded and replaced by new probes after each measurement. However, probes for continuously measuring the oxygen content of molten metal are also known. One example of such probes is the one disclosed in Canadian Pat. No. 990,352 issued June 1st, 1976. The oxygen probe disclosed in the above patent consists of a solid electrolyte tube encased in a stainless steel tube and is capable of withstanding the operative conditions of the molten metal for a substantial length of time but, nevertheless, has a limited life time.

It is the object of the present invention to provide an oxygen monitoring circuit which includes means for detecting aging of the oxygen probe and warning an operator of impending probe failure as the probe approaches the end of its normal life time.

The oxygen monitoring circuit, in accordance with the invention, comprises a high impedance follow and hold circuit adapted for connection to an oxygen probe, a readout unit connection to the high impedance follow and hold circuit, a programmer connecting the oxygen probe to the high impedance follow and hold circuit but momentarily disconnecting the oxygen probe from said high impedance follow and hold circuit for a relatively short time interval and loading it with a resistor having an impedance relatively higher than that of the probe, and a probe failure indicator connected to the output of the oxygen probe and of the high impedance follow and hold circuit for detecting any significant change in impedance of the probe and resistor combination as a result of loading and for operating an alarm when the impedance of the probe exceeds a predetermined value.

The high impedance follow and hold circuit preferably comprises a high impedance voltage follower adapted to hold the last measured voltage of the probe representing the oxygen content of the molten metal during the time when the oxygen probe is disconnected from the high impedance follow and hold circuit.

The programmer preferably includes a timing circuit normally providing an output voltage of a predetermined value but momentarily switching such voltage to zero during the relatively short time interval when the probe is loaded with the resistor, a first relay which is switched on by the timing circuit when its output is high for operating a set of normally open contacts to connect the oxygen probe to the high impedance follow and hold circuit, and which is switched off by the timing circuit when its output is zero to disconnect the oxygen probe from the high impedance follow and hold circuit, and a second relay which is switched on by the timing circuit when its output is zero for connecting the resistive load to the oxygen probe. Means are also preferably provided for delaying the operation of the second relay for a short time interval after the output of the timing circuit is switched to zero so as to make sure that the high impedance follow and hold circuit is disconnected from the oxygen probe before loading the probe with the resistor.

The probe failure indicator may comprise a high impedance voltage follower connected to the oxygen probe and a voltage comparator connected to the output of the voltage follower and the output of the follow and hold circuit for comparing the loaded and unloaded probe voltages, a switching device connected to the output of the voltage comparator, and an indicator device connected to the switching device for providing an alarm when the loaded probe voltage falls below a predetermined fraction of the unloaded probe voltage.

A high-low oxygen limit indicator may also be connected to the output of the high impedance follow and hold circuit for indicating when high or low ppm oxygen limits are reached.

The output voltage of oxygen probes is normally a logarithmic function of the oxygen content of the molten metal. Therefore, an antilog conversion circuit is preferably connected between the output of the follow and hold circuit and the readout device for converting the normal logarithmic output of the oxygen probe to a linear output which can be more easily shown on the readout device. A variable voltage reference source is also preferably provided for periodic checking of the antilog conversion circuit.

The oxygen probe monitoring circuit may also be provided with a thermocouple probe immersed in the molten metal, a thermocouple signal conditioner connected to the thermocouple probe, and means for connecting the output of the thermocouple probe to the readout device.

The invention will now be disclosed, by way of example, with reference to the accompanying drawings in which.

Figure 1:
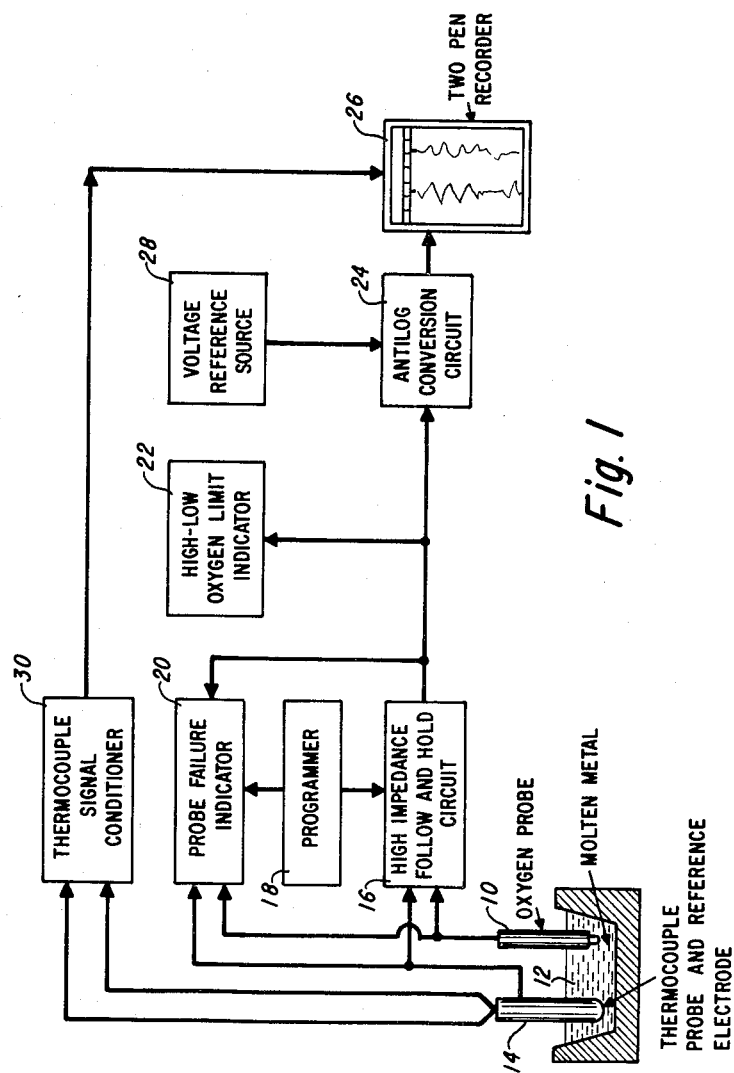
FIG. 1 illustrates a block diagram of a monitoring circuit in accordance with the invention.

Referring to the drawings, FIG. 1 is a block diagram of an embodiment of a monitoring circuit in accordance with the invention shown in combination with a diagrammatic illustration of an oxygen probe 10 immersed in molten metal 12. The probe system is also provided with a thermocouple probe 14 the outside shell of which also acts as a reference electrode for the oxygen probe 10.

The output of the oxygen probe 10 is applied to a high impedance follow and hold circuit 16 which is controlled by a programmer 18. As it will be clearly disclosed later, the high impedance follow and hold circuit 16 is normally connected to the output of the oxygen probe but is disconnected at regular intervals by the programmer 18 for momentarily testing the probe. During testing of the probe, the last reading made by the probe is held by the follow and hold circuit until the probe is connected back to the follow and hold circuit.

The output of the oxygen probe is also applied to a probe failure indicator 20 which provides an alarm when the probe is about to fail. The probe failure indicator is responsive to the programmer 18 during testing of the probe for detecting an increase in impedance of the probe as an indication of impending probe failure.

The output of the high impedance follow and hold circuit is applied to a high and low oxygen limit indicator 22 and, more importantly, to an antilog conversion circuit 24 which converts the normal logarithmic output of the probe to a linear output which is applied to a recorder 26. A voltage reference 28 is also provided for testing the antilog conversion circuit.

The output of the thermocouple probe 14 is applied to a thermocouple signal conditioner 30 the output of which is applied to recorder 26. Recorder 26 is advantageously a two pen type for indicating and recording both the oxygen content and the temperature of the molten metal. Of course, two separate readout devices could be used.

Figure 2:
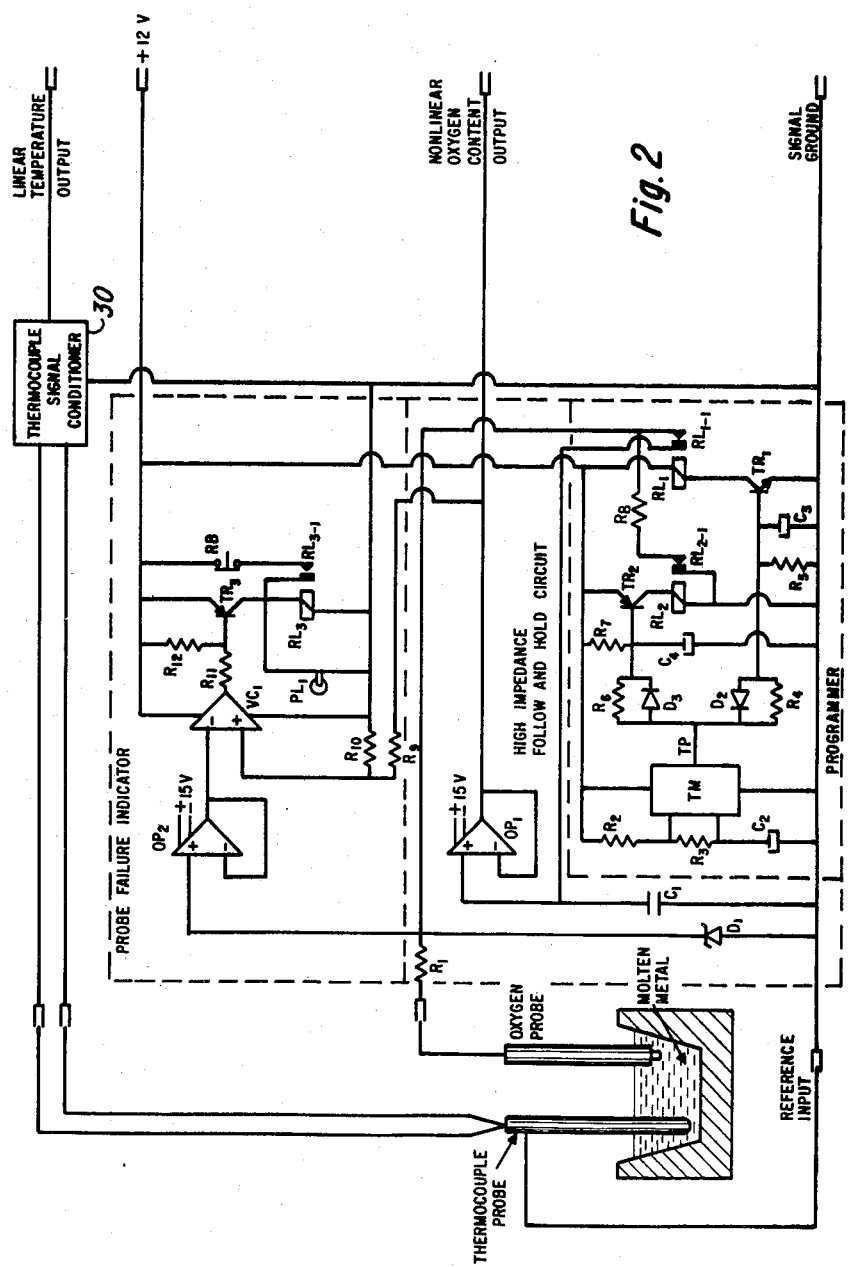
FIGS. 2 and 3 illustrate a circuit diagram of the monitoring circuit shown in schematic form in FIG. 1.
Figure 3:
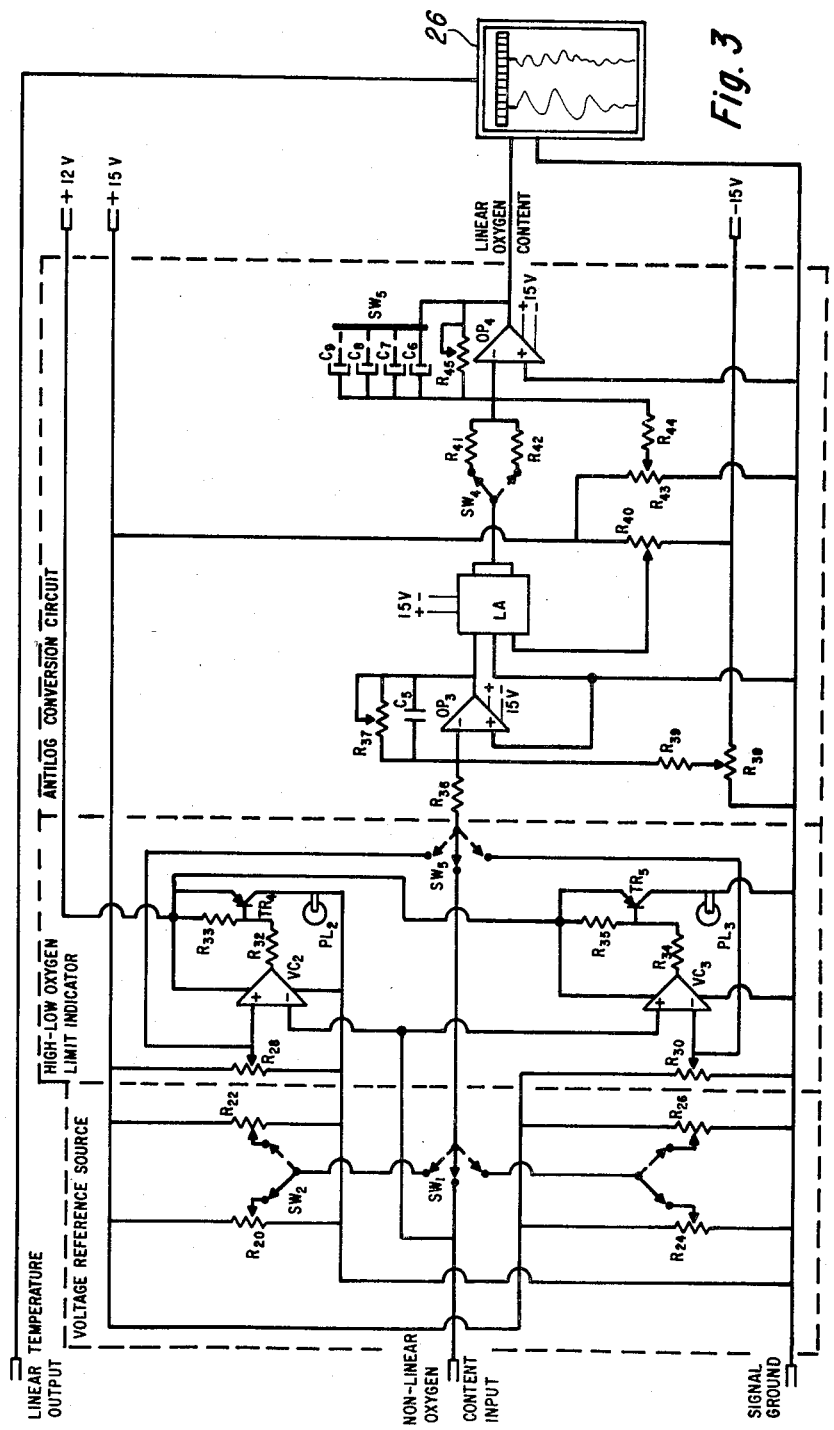

FIGS. 2 and 3 illustrate a circuit diagram of the monitoring circuit shown in schematic form in FIG. 1. The output of the probe is fed to the non-inverting input terminal of an operational amplifier OPI through a resistor R1 and normally open contacts RL1-1 of a relay RL1 to be disclosed later. Operational amplifier OP1 is connected as a voltage follower and has a high input impedance. Resistor R1 has a negligible impedance value with respect to the probe impedance. A zener diode D1 is connected across the non-inverting terminal of the operational amplifier and ground to protect the operational amplifier in case of overvoltage. A capacitor C1 is connected between the non-inverting terminal of the operational amplifier and ground to hold the voltage applied to the non-inverting terminal of the operational amplifier when contacts RL1-1 are open during testing of the probe as it will be more clearly disclosed later.

Figure 4:
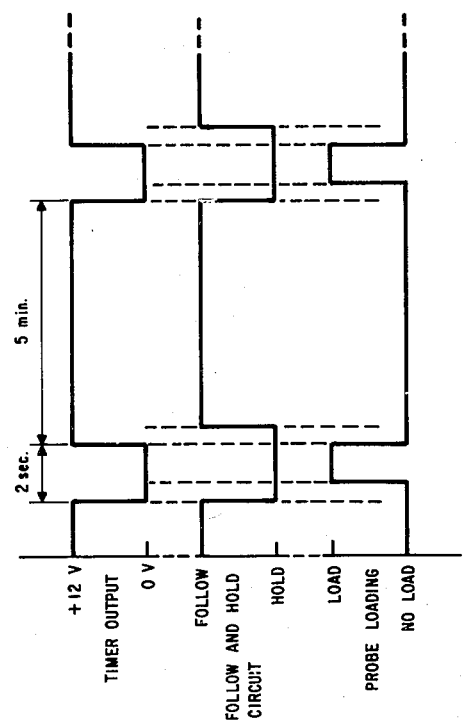
FIG. 4 illustrates the timing cycle of the programmer shown in FIG. 2.

The programmer 18 includes, as main components, a conventional timer TM operated by a 12 V reference source, transistors TR1 and TR2 and relays RL1 and RL2. A suitable timer integrated circuit may be Model No. NE 555 made by SIGNETICS. The timing cycle of the timer is shown in FIG. 4 of the drawings and is controlled by resistors R2 and R3 and a capacitor C2 forming part of the timer. When the output TP of the timer is high (12 V in this case), transistor TR1 is biased into conduction through series resistor R4 and parallel connected resistor R5 and capacitor C3. Relay RL1 which is connected in series with the collector emitter electrodes of transistor TR1 across the 12 V reference source is energized to close its contacts RL1-1. The output of the probe is thus applied to the non-inverting input terminal of the operational amplifier OP1. During that time, the high potential appearing at the output TP of the timer is also applied to the base of transistor TR2 through resistor R6. However, transistor TR2 is maintained non-conductive by a capacitor C4 connected to the base of the transistor and charged to the voltage of the 12 V reference source through a resistor R7. Relay RL2 which is connected in series with the emitter and collector electrodes of transistor TR2 across the 12 V reference source is not energized and contacts RL2-1 of relay RL2 remain open.

When the output TP of the timer goes down to zero, capacitor C3 is instantaneously discharged through a diode D2 connected across resistor R4 and transistor TR1 is cut-off. Relay RL1 is released and contacts RL1-1 are opened. At the same time, capacitor C4 discharges through resistor R6 and, after a slight delay, transistor TR2 becomes conductive. Relay RL2 is energized and contacts RL2-1 of relay RL2 are closed to connect a resistor R8 across the oxygen probe. The impedance of resistor R8 is selected high enough as compared to the normal impedance of the probe so that it will not influence significantly the reading of the probe when the probe is good, but will when the probe is about to fail and its impedance approaches that of the resistor R8. The slight delay introduced into the operation of relay RL2 after release of relay RL1 insures that the output of the probe is disconnected from the input of the operational amplifier OP1 before loading of the probe so that, if there is any influence on the output of the probe by such loading, it will not appear at the input of the recorder 26.

When the output TP of the timer goes back to high, transistor TR2 is instantaneously rendered non-conductive by a diode D3 connected resistor R6 which charges up quickly capacitor C4 and relay RL2 is released, opening its contacts RL2-1. After a short delay, as determined by the charging time of capacitor C3, transistor TR1 is rendered conductive again and relay RL1 is energized to close contacts RL1-1 and connect the output of the probe to the high impedance follow and hold circuit.

The output of the probe is also applied to the non-inverting input terminal of an operational amplifier OP2 of the probe failure indicator. The operational amplifier OP2 is connected as a voltage follower. The output of the operational amplifier is applied to the inverting input terminal of a voltage comparator VC1. A predetermined offset potential, which may be about 70% of the non-loaded value of the output of the high impedance follow and hold circuit as determined by the relative values of resistors R9 and R10, is applied to the non-inverting input terminal of the voltage comparator VC1. The output of the voltage comparator VC1 is applied to the base of a transistor TR3 through a resistor R11. A resistor R12 is connected between the emitter and base of transistor TR3. A relay RL3 is connected in series with the emitter and collector electrodes of transistor TR3 across the 12 V reference source. When loading of the probe with resistor R8 changes the output of the probe by more than, say 30%, due to a significant increase in the impedance of the probe caused by aging, the voltage comparator provides an output which biases transistor TR3 into conduction. Relay RL3 and a pilot light PL1 connected across relay RL3 are energized. Contacts RL3-1 of relay RL3 are closed to lock the pilot light across the 12 V reference until release button RB is operated.

The thermocouple signal conditioner 30 is a conventional device such as Model No. 4100-1298 made by Action Instruments Co. It is used to linearize and expand the temperature scale in the range of 1800°–2300° F., which is a practical temperature range for copper casting. Such a temperature will be indicated on a scale of the readout device 26 and recorded by one of the pens of the recorder.

Figure 5:
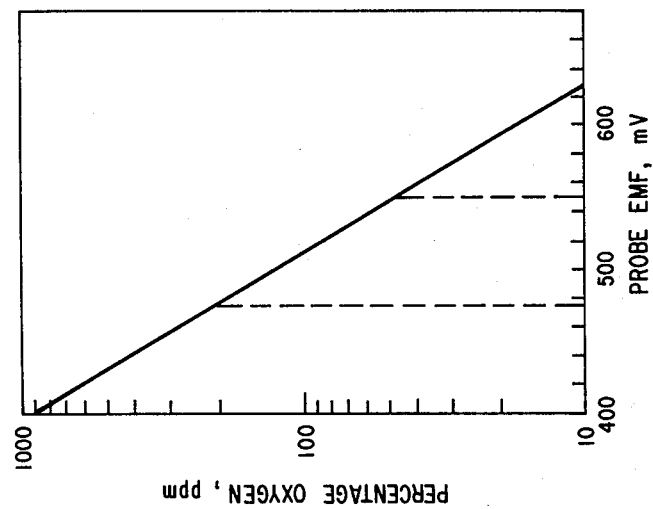
FIG. 5 illustrates the output of a probe which may be used in conjunction with the monitoring circuit in accordance with the invention.

FIG. 3 illustrates a circuit diagram of the voltage reference source 28 shown in FIG. 1. Potentiometers R20 and R22 are connected across a 15 V reference source and used to preset upscale set points for the 0–250 and 0–500 ppm oxygen ranges, respectively. Potentiometers R24 and R26 are also connected to the 15 V reference source and used to preset downscale set points for the 0–250 and 0–500 ppm oxygen ranges, respectively. The above set points are used for periodic checking of the antilog conversion circuit. A convenient value for a downscale set point might be 546 mV corresponding to 50 ppm oxygen in the molten metal as measured by an oxygen probe as disclosed in the above mentioned Canadian Pat. No. 990,352 the output of which is shown in FIG. 5. Similarly, a convenient value for an upscale set point may be 475 mV corresponding to 200 ppm oxygen. The chosen set points are selected by switch SW1. Switches SW2, SW3 and SW4 are all ganged together for the selection of the 0-250 or the 0-500 ppm oxygen range.

FIG. 3 also illustrates a circuit diagram of a suitable high-low oxygen limit indicator shown at 22 in FIG. 1. The output of the probe is applied to the inverting input terminal of a voltage comparator VC2 and to the non-inverting input terminal of a voltage comparator VC3. The high limit for voltage comparator VC2 is set by a potentiometer R28 connected across the 15 V reference source whereas the low limit for voltage comparator VC3 is set by a potentiometer R30 also connected to the 15 V reference source. The output of voltage comparator VC2 is connected to the base of a transistor TR4 through a resistor R32. A resistor R33 is also connected between the emitter and base of transistor TR4. A pilot light PL2 is connected in series with the emitter and collector electrodes of transistor TR4 across a 12 V reference source. Whenever the upper oxygen limit is exceeded, voltage comparator VC2 provides an output current to the base of transistor TR4 through resistor R32 to render the transistor conductive and operate the pilot light PL2.

The output of voltage comparator VC3 is applied to the base of a transistor TR5 through a resistor R34. A resistor R35 is also connected between the emitter and base of transistor TR5. A pilot light PL3 is connected in series with the emitter and collector electrodes of transistor TR5 across the 12 V reference source. Whenever the lower oxygen limit is reached, voltage comparator VC3 provides an output current to the base of transistor TR5 through resistor R34 to render transistor TR5 conductive and operate the pilot light PL3. The set points of resistors R28 and R30 may be checked on the readout device through switch SW5.

FIG. 3 also discloses the circuit diagram of a suitable antilog conversion circuit which is shown schematically at 24 in FIG. 1. In this embodiment, a Teledyne Phillick No. 4351 logarithmic amplifier has been used although other antilog modules could be used. In this amplifier, designated by reference LA, the input decade selected goes from 0.1 to 1.0 V. In order to match a decade of say 50-500 ppm oxygen in the molten metal (which gives a corresponding voltage value of 546-430 mV at the output of a probe as disclosed in the above mentioned Canadian Pat. No. 990,352 and shown in FIG. 6) an operational amplifier OP3 is used to amplify the output of the probe and to match it to the decade input of the antilog module. The output of the probe as it appears at the output of the high impedance follow and hold circuit is fed to the inverting input terminal of operational amplifier OP3 through a resistor R36. A variable resistor R37 is connected across the inverting input terminal and the output terminal of the operational amplifier OP3 to provide adjustment for the required amplification. A capacitor C5 is connected across resistor R37 for filtering transients. A potentiometer R38 is connected across a −15 V reference source and has its variable tap connected to the inverting terminal of the operational amplifier through a resistor R39 to provide the required offset for the operational amplifier. The antilog module LA is also provided with a trimming resistor R40 which is connected between the +15 V reference source and the −15 V reference source to make the final adjustments.

When the above logarithmic amplifier is operated in the input range of 0.1 to 1 V, its linear output voltage varies from −10 to −79.4 mV. The recorder used in the present invention operates in the range of 0-1000 mV and it is thus required to amplify the output voltage of the logarithmic amplifier by a predetermined factor so that the maximum output going to the recorder will be 1000 mV. This amplification is done by an operational amplifier OP4. Resistors R41 and R42 are selected in the ratio of 1:2 and are selectively engaged by switch SW4, depending on the ppm oxygen range being measured, to connect the output of the logarithmic amplifier LA to the inverting input terminal of the operational amplifier OP4. Operational amplifier OP4 is also used to adjust the offset so that the output of the operational amplifier will be 0-1 V for a measured oxygen range of 0-250 or 0-500 ppm. The offset is regulated by a potentiometer R43 which is connected between ground and the +15 V reference source and has its variable tap connected to the non-inverting input terminal of the operational amplifier through a resistor R44. A variable resistor R45 is connected across the inverting input terminal and the output terminal of the operational amplifier OP4 in order to provide means for final gain adjustment. Capacitors C6-C9 of incremental capacitance value are connected across the resistor R45 for providing an averaging effect and filtering of the transients passing through the instrument. The proper capacitor is selected by selector switch SW5.

As it will be obviously seen from the above description, the oxygen probe is loaded at regular intervals with resistor R8. If any significant increase in the impedance of the probe occurs, this will be detected and shown by the probe failure indicator as an indication of impending probe failure. During loading of the probe, the previous ppm oxygen level is held by the high impedance follow and hold circuit. The loading time interval is very short (i.e. about 1 second) as compared to the intervals between loadings (i.e. about five minutes).

The logarithmic output of the probe is converted to a linear function by the antilog conversion circuit so that it may be easy to read on a linear scale readout device.

The monitoring circuit is also conveniently provided with a high-low oxygen limit indicator as well as an adjustable reference source for calibrating the antilog conversion circuit.

Although the invention has been disclosed with reference to a preferred embodiment, it is to be understood that it is not limited to such embodiment. For example, other types of high impedance follow and hold circuit, readout unit, programmer and probe failure indicator could be used.

The embodiments of the invention in which an exclusive property or privilege is claimed are defined as follows:

1. An oxygen monitoring circuit adapted for connection to an oxygen probe immersed in molten metal comprising:
   (a) a high impedance follow and hold circuit adapted for connection to the oxygen probe;
   (b) a readout unit connected to the high impedance follow and hold circuit;
   (c) a programmer normally connecting said oxygen probe to said high impedance follow and hold circuit but momentarily disconnecting the oxygen probe from said high impedance follow and hold circuit for a relatively short time interval and loading it with a resistor having an impedance relatively higher than the normal impedance of the oxygen probe; and (d) a probe failure indicator connected to the output of said oxygen probe and to the output of said high impedance follow and hold circuit for detecting any significant change in impedance of the probe and resistor combination as a result of loading and for operating an alarm when the impedance of the probe exceeds a predetermined value.

2. An oxygen monitoring circuit as defined in claim 1, wherein said high impedance follow and hold circuit comprises a high impedance voltage follower adapted to hold the last measured output voltage of the oxygen probe corresponding to the oxygen level in the molten metal during the time that the oxygen probe is disconnected from the high impedance follow and hold circuit.

3. An oxygen probe monitoring circuit as defined in claim 1, wherein said programmer includes a timing circuit normally providing an output voltage of predetermined value but momentarily switching said voltage to zero during the relatively short time interval when the probe is loaded with said resistor, a first relay which is switched on by said timing circuit when its output is high for operating a set of normally open contacts to connect said oxygen probe to said high impedance follow and hold circuit and which is switched off by said timing circuit when its output is zero to disconnect the oxygen probe from the high impedance follow and hold circuit, and a second relay which is switched on by said timing circuit when its output is zero for connecting said high impedance load to the oxygen probe.

4. An oxygen monitoring circuit as defined in claim 3, further comprising means for delaying the operation of said second relay for a short time interval after the output of said timing circuit has switched to zero so as to make sure that the high impedance follow and hold circuit is disconnected from the oxygen probe before loading the probe with said resistor.

5. An oxygen monitoring circuit as defined in claim 1, wherein said probe failure indicator comprises a high impedance voltage follower connected to said oxygen probe, a voltage comparator connected to the output of said voltage follower and to the output of the follow and hold circuit for comparing the loaded and unloaded probe voltages, a switching device connected to the output of said voltage comparator, and an indicator device connected to said switching device for providing an alarm when the loaded probe voltage falls below a predetermined fraction of the unloaded probe voltage.

6. An oxygen monitoring circuit as defined in claim 1, further comprising a high-low oxygen limit indicator connected to the output of said high impedance follow and hold circuit for indicating when high or low ppm oxygen limits are reached.

7. An oxygen monitoring circuit as defined in claim 1, wherein the output voltage of the oxygen probe is a logarithmic function of the oxygen content of the molten metal, and further comprising an antilog conversion circuit interconnecting said high impedance follow and hold circuit to said readout device for converting the normal logarithmic output of the oxygen probe to a linear output.

8. An oxygen monitoring circuit as defined in claim 7, further comprising a variable voltage reference source for testing said antilog conversion circuit.

9. An oxygen monitoring circuit as defined in claim 1, further comprising a thermocouple probe immersed in the molten metal, a thermocouple signal conditioner connected to said thermocouple probe, and means for connecting the output of said thermocouple conditioner to said readout device.

10. An oxygen monitoring circuit as defined in claim 9, wherein said readout device is a two pen recorder for recording both temperature and the oxygen content of the molten metal.

* * * * *